US006954952B1

(12) United States Patent
Kroupa

(10) Patent No.: US 6,954,952 B1
(45) Date of Patent: Oct. 18, 2005

(54) BACKBOARD

(75) Inventor: Kevin D. Kroupa, Ballwin, MO (US)

(73) Assignee: Allied Healthcare Products, Inc., St. Louis, MO (US)

(*) Notice: Subject to any disclaimer, the term of this patent is extended or adjusted under 35 U.S.C. 154(b) by 0 days.

(21) Appl. No.: 10/867,327

(22) Filed: Jun. 14, 2004

(51) Int. Cl.[7] ............................ A61G 1/00; A61B 6/04
(52) U.S. Cl. ............................... 5/625; 5/601; 378/209
(58) Field of Search ..................... 5/625, 601; 378/209

(56) References Cited

U.S. PATENT DOCUMENTS 4,893,323 A 1/1990 Cook, III
4,926,457 A 5/1990 Poehner et al.
4,949,713 A 8/1990 Mykietiuch
5,048,136 A 9/1991 Popitz
5,263,213 A 11/1993 Robertson et al.
D358,652 S 5/1995 Pretzer
5,473,784 A 12/1995 Nixon et al.
5,568,662 A * 10/1996 Gougelet ........................ 5/625
5,742,963 A 4/1998 Trevino et al.
5,765,243 A 6/1998 Duncan et al.
5,771,513 A 6/1998 Kirchgeorg et al.
5,774,916 A 7/1998 Kurhi
D403,423 S 12/1998 Bologovsky et al.
5,950,627 A 9/1999 Bologovsky et al.
6,067,678 A 5/2000 Trevino
2004/0187214 A1 * 9/2004 Holland ......................... 5/626

* cited by examiner

*Primary Examiner*—Robert G. Santos
(74) *Attorney, Agent, or Firm*—Ari M. Bai; Greensfelder, Hemker & Gale, P.C.

(57) ABSTRACT

The present invention relates to a structurally rigid, X-ray translucent backboard for transporting an injured person from the scene of an injury to a treatment center. The backboard comprises a planar top side which contacts the patient and a bottom side forming a single curvilinear shape that provides structural support to the planar top side. A hollow, foam filled core formed between the planer top side and the curved bottom side helps provide sufficient X-ray translucence and structural support to the backboard.

20 Claims, 5 Drawing Sheets

| Deflection at Various Loads (in Inches) | | | | | | | | |
|---|---|---|---|---|---|---|---|---|
| | Supported at Two Points | | | | Supported at Four Points | | | |
| **Backboard** | **100 lbs.** | **Difference** | **200 lbs.** | **Difference** | **300 lbs.** | **Difference** | **400 lbs.** | **Difference** |
| Backboard 10 | 1.530 | | 2.438 | | .14 | | .241 | |
| Prior Art 1 | 1.725 | 0.195 | 2.800 | 0.362 | 0.814 | 0.674 | 1.042 | 0.801 |
| Prior Art 2 | 2.031 | 0.501 | 3.254 | 0.816 | 1.035 | 0.895 | 1.280 | 1.039 |
| Prior Art 3 | 1.872 | 0.342 | 3.061 | 0.623 | 0.691 | 0.551 | 0.998 | 0.757 |
| Prior Art 4 | 2.27 | 0.740 | 3.527 | 1.089 | 1.014 | 0.874 | 1.381 | 1.140 |
| Prior Art 5 | 1.474 | (0.056) | 2.295 | (0.143) | 0.686 | 0.546 | 0.863 | 0.622 |
| Prior Art 6 | 0.060 | (1.470) | 2.324 | (0.114) | 0.099 | (0.041) | 0.193 | (0.048) |
| Prior Art 7 | 1.140 | (0.390) | 1.576 | (0.862) | 0.313 | 0.173 | 0.492 | 0.251 |
| Prior Art 8 | 1.167 | (0.363) | 1.660 | (0.778) | 0.357 | 0.217 | 0.581 | 0.340 |

Fig. 4

BACKBOARD

BACKGROUND OF THE INVENTION

1. Field of the Invention

The present invention relates to an improved backboard for transporting a patient.

2. Prior Art

Backboards may be used to transport patients who have suffered severe trauma, such as a spinal cord injury, that may develop into partial or total paralysis if the patient is moved improperly. Therefore, it is imperative that backboards have sufficient rigidity with a low rate of deflection and not flex or bend under the patient's weight in order to prevent unnecessary patient movement. To further minimize the patient's movement, it may be desirable that the patient remain on the backboard when being X-rayed at a treatment center. However, if the patient remains on the backboard when being X-rayed, the backboard must be substantially X-ray translucent in order to enable a high quality, medically acceptable X-ray of the patient to be obtained.

However, prior art backboards either have a high degree of X-ray translucence while not being substantially stable, or are structurally stable without being sufficiently X-ray translucent. In particular, backboards of the prior art that are completely planar on both sides have a high degree of X-ray translucence, but are not sufficiently rigid when supporting a patient due to a lack of structural supporting members located within the board. Other prior art backboards may provide structural strength by providing supporting members within the backboard or by molding a series of ridges into the bottom side of the backboard. Although these design features provide structural rigidity, the stiffening rods and/or molded ribs appear on X-rays and can adversely affect the backboard's X-ray translucence.

Therefore, there appears a need in the art for a backboard that is lightweight, cost effective to manufacture, and sufficiently rigid to adequately support a patient while being substantially X-ray translucent.

OBJECTS AND SUMMARY OF THE INVENTION

Accordingly, the primary object of the present invention is to provide a lightweight, sufficiently rigid backboard for patient transport that is substantially X-ray translucent and inexpensive to manufacture.

Another object of the present invention is to provide a substantially X-ray translucent, lightweight backboard that has enough structural rigidity to support a patient without undue flexing or bending of the backboard under the patient's weight during transport.

A further object of the present invention is to provide a substantially X-ray translucent backboard that is constructed from a unitary piece of material with an interior core filled with an X-ray translucent material.

Yet another object of the present invention is to provide a sufficiently rigid backboard that does not require stiffening members or the like which may reduce the X-ray translucence of the backboard.

Another further object of the present invention is to provide a backboard having a continuous curvilinear shape along one side thereof that provides substantial X-ray translucence and structural rigidity.

These and other objects of the present invention are realized in the preferred embodiment of the present invention, described by way of example, and not by way of limitation, which provides for a rigid, substantially X-ray translucent backboard comprising a single curvilinear shaped bottom surface and an opposing planar top surface that contacts a patient with a foam-filled supporting member formed therebetween.

In brief summary, the present invention overcomes and substantially alleviates the deficiencies in the prior art by providing a sufficiently rigid and substantially X-ray translucent backboard for transporting a patient. The improved backboard comprises a planar top surface adapted to contact the patient that is structurally supported by an opposing curvilinear shaped bottom surface. Specifically, the bottom surface has a single curvilinear shape that extends the entire length of the backboard in order to provide sufficient structural support, while forming an angular orientation which provides substantial X-ray translucence to the backboard. In addition, a foam material fills the interior space between the upper planar surface and the curvilinear shaped bottom surface that allows the backboard to remain lightweight and inexpensive to manufacture without sacrificing either the X-ray translucence or structural rigidity of the backboard.

Additional objects, advantages, and novel features of the invention will be set forth in the description that follows and will become apparent to those skilled in the art upon examination of the following more detailed description and drawings in which like elements of the invention are similarly numbered throughout.

BRIEF DESCRIPTION OF THE DRAWINGS

FIG. 4 is a table comparing the deflection rates of the backboard of the present invention to several prior art backboards.

DETAILED DESCRIPTION OF THE INVENTION

Figure 1:
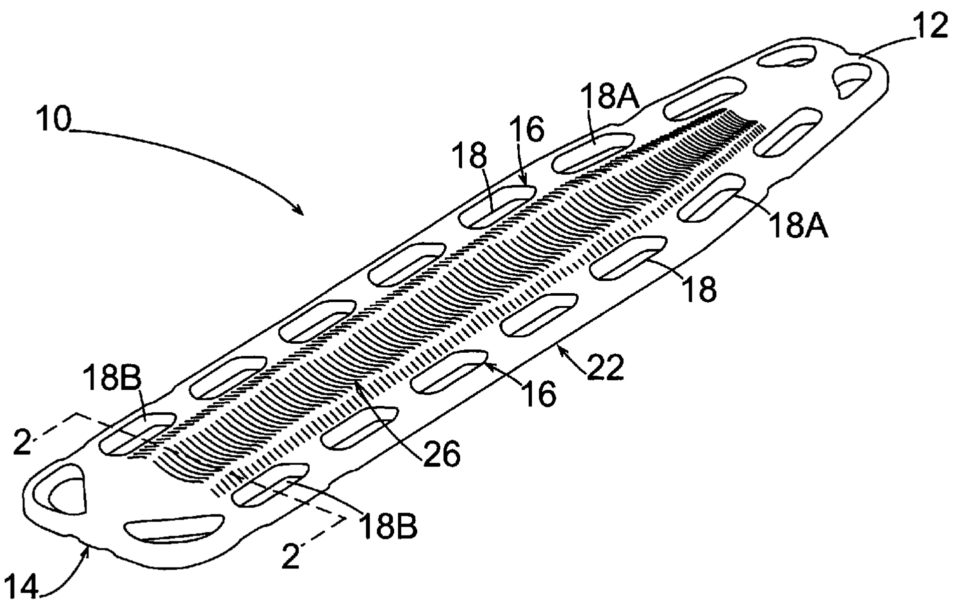
FIG. 1 is a perspective view of the backboard depicting the single curvilinear shaped bottom surface according to the present invention.

Referring to the drawings, the preferred embodiment of the backboard is illustrated as 10 in FIG. 1. Backboard 10 according to the present invention provides a means for transporting a patient that has a high degree of structural rigidity, while being substantially X-ray translucent.

As shown, backboard 10 comprises a unitary, substantially rectangular shaped member that defines a front portion 12, a rear portion 14, two opposing side portions 16, and opposing top and bottom sides 20 and 22. Top side 20 provides a planar top surface adapted for supporting a patient and a single, continuous curvilinear shaped bottom side 22 with a hollow core 24 formed therebetween. In the preferred embodiment, hollow handles 18 are integrally formed along opposing side portions 16, front portion 12, and rear portion 14 that enable backboard 10 to be easily handled by one or more persons. Preferably, backboard 10 may be 71" long as measured from front portion 12 to rear portion 14 and 15.75" inches wide as measured from one side portion 16 to the opposing side portion 16. However, the present invention contemplates that any suitable length and width of backboard 10 that is substantially x-ray translucent and structurally rigid is felt to fall within the scope of the present invention.

Figure 2:
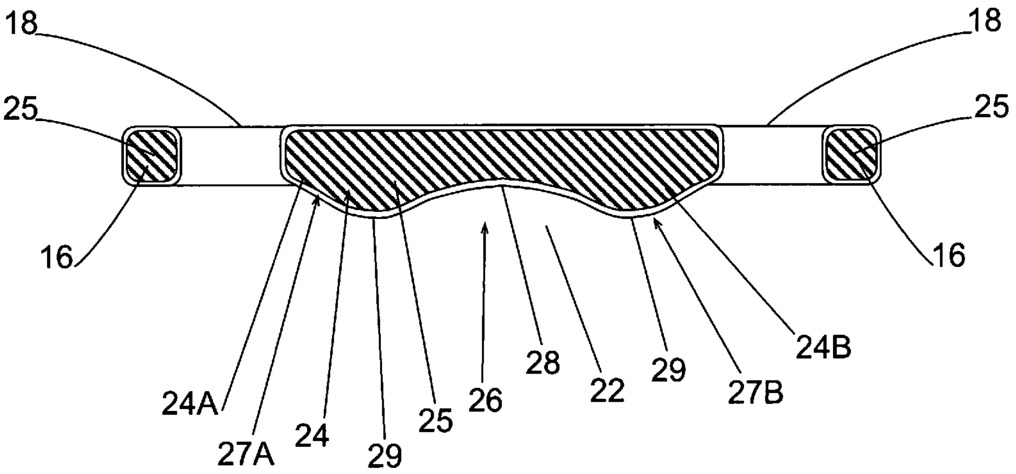
FIG. 2 is a cross-sectional view taken along line 2—2 of FIG. 1 depicting the single curvilinear shaped bottom surface and planar top surface defining an interior portion filled with foam according to the present invention.
Figure 3:
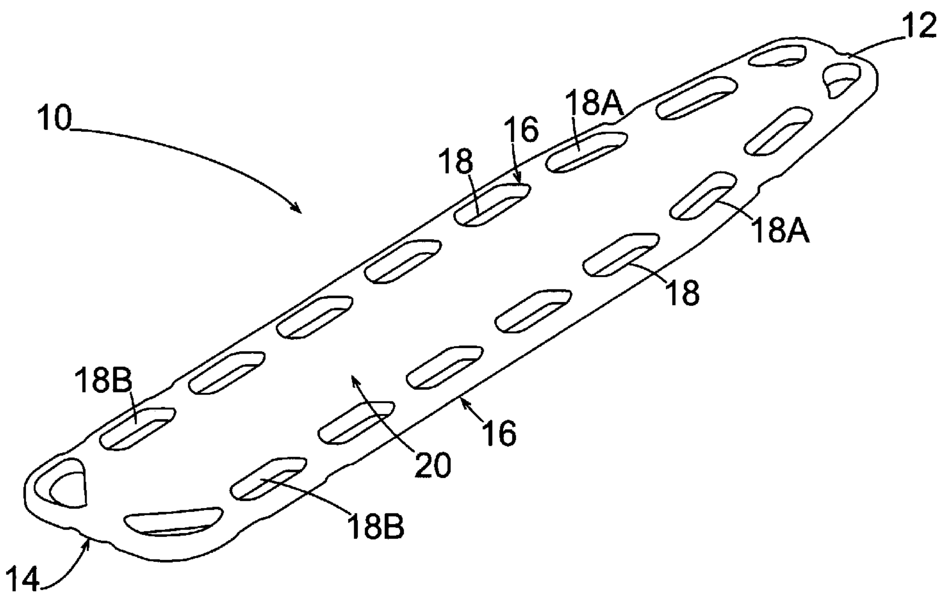
FIG. 3 is a perspective view of the backboard depicting the opposing planar top surface according to the present invention.

Referring to FIG. 2, hollow core 24 is preferably filled with a foam material 25 which permits backboard 10 to be extremely lightweight and sufficiently rigid while remaining substantially X-ray translucent. The applicant defines the language "substantially X-ray translucent" herein to mean that structural element(s) of backboard 10 other than a faint outline of the body of the backboard 10 will not appear in a medically acceptable X-ray of the patient being supported by backboard 10. Specifically, this level of substantial X-ray translucence is completely free of all foreign artifacts, such as supporting rods, ridges, other objects, or design elements used to provide structural support to prior art backboards. Foam material 25 also enables backboard 10 to float and support a person weighing up to 70 pounds fully above water. Preferably, backboard 10 is capable of maintaining the face of a two hundred pound person above water and can also be used as a water rescue device, if desired. The use of foam material 25 is highly advantageous because the nature of the material contributes to the substantial X-ray translucent nature of backboard 10. Preferably, a light weight foam material 25 is utilized, however, the present invention contemplates that any suitable X-ray translucent material inside hollow core 24 is felt to fall within the scope of the present invention.

Referring back to FIGS. 1 and 2, bottom side 22 forms a curvilinear portion 26 extending from front portion 12 to rear portion 14 of backboard 10. Curvilinear portion 26 is formed from first and second symmetrical curved sides 27A and 27B having a trough 28 formed between opposed peaks 29. Preferably, the angle between each peak 29 and trough 28 of curvilinear portion 26 is 45°, although the present invention contemplates that other angular orientations between peak 29 and trough 28 may be in the range of between 30°–60°, although any suitable angular orientation that does not interfere with the substantial X-translucence of backboard 10 is felt to fall within the scope of the present invention. The angular orientation of curvilinear portion 26 is configured to make backboard 10 substantially X-ray translucent, yet provide sufficient structural support to top side 20 as explained in greater below.

As further shown, curvilinear portion 26 comprises structural regions 24A and structural region 24B that extend from front portion 12 to rear portion 14 of backboard 10 and extend parallel to trough 28. Preferably, both structural region 24A and structural region 24B are positioned equidistant relative to trough 28. Since hollow core 24 is completely filled with foam 25, structural regions 24A and 24B contain significantly more foam 25 than the portion of hollow core 24 located directly above peak 28. Accordingly, the extra mass of foam 25 within structural region 24A and structural region 24B provides improved structural support to backboard 10 due to the extra mass of foam 25 along equidistant locations from trough 28. It has been found that the curvilinear portion 26 also provides backboard 10 with a structural strength and rigidity having a low deflection rate capable of supporting a 1000-pound load when carried by four people as discussed below. This low deflection rate is extremely advantageous because it shows that the patient will not bend or deflect the body of backboard 10 and is therefore not subjected to unnecessary movement when transported.

This low deflection rate is measured along the middle of the body of backboard 10 in inches as depicted in FIG. 4. As shown, when backboard 10 is used to transport a one hundred pound patient and is carried by two people along front and rear portions 12 and 14, respectively, backboard 10 has been found to have a deflection rate of only 1.53 inches. The deflection rate for a 200 pound patient has been found to be 2.43 inches when backboard 10 is similarly supported by two people along front and rear portions 12 and 14.

It has also been found that if backboard 10 is carried by four people, the deflection rates are even further reduced as illustrated in FIG. 4. Preferably, four people hold backboard 10 by grasping a specific set of handles 18 denoted as 18A and 18B located along side portions 16. For example, two people could each hold handles 18A and two other people could grasp handles 18B to achieve the lower deflection rates found in FIG. 4.

Figure 5:
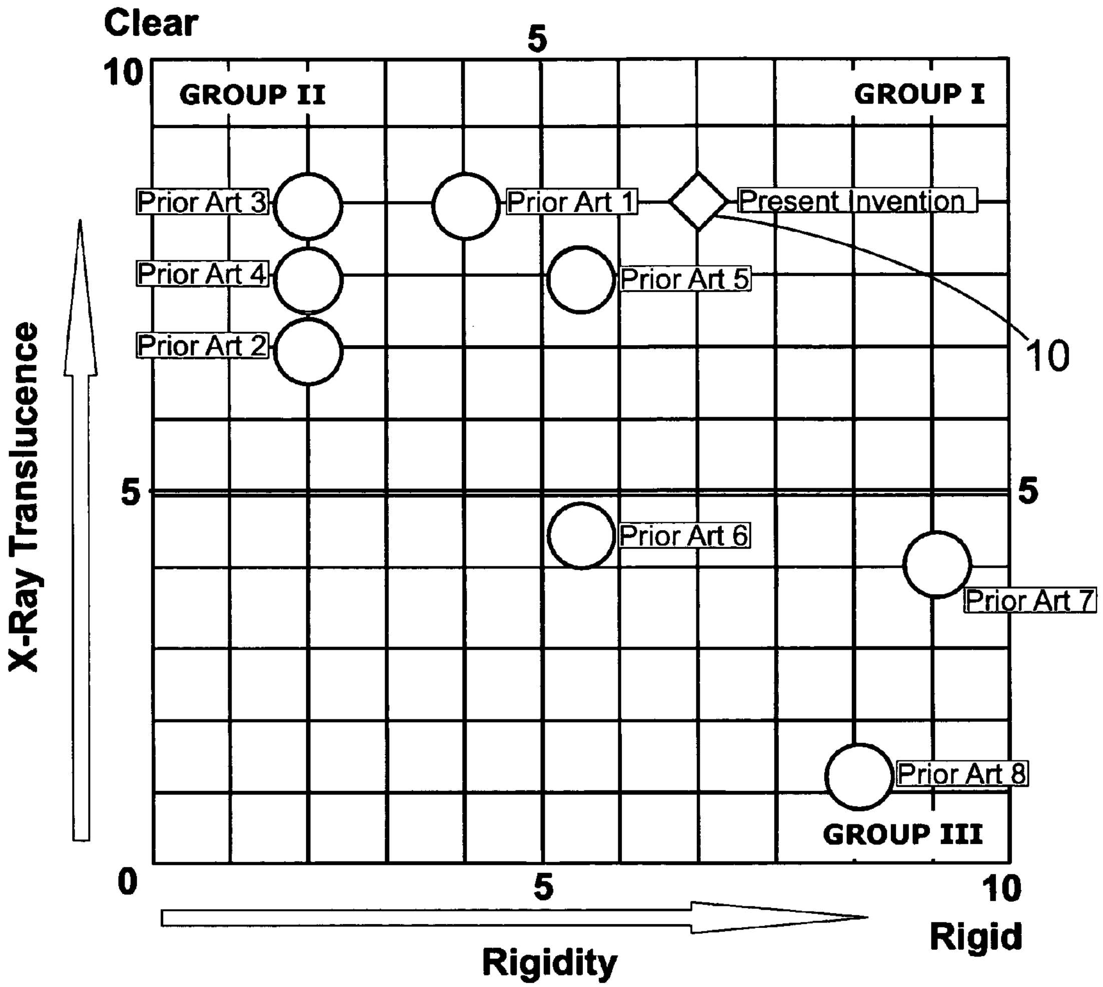
FIG. 5 is a graph illustrating rigidity vs. X-ray translucence of the backboard according to the present invention relative to other prior art backboards noted in FIG. 4.

As can be seen in FIG. 5, the increased rigidity of backboard 10 does not hinder its substantially X-ray translucent nature. FIG. 5 is a graph that compares the X-ray translucence of backboard 10 with the prior art backboards noted in FIG. 4. As shown, backboard 10 is the most structurally rigid and X-ray translucent backboard compared to the prior art backboards. Therefore, backboard 10 is capable of being substantially X-ray translucent while maintaining a high degree of structural rigidity.

It should be understood from the foregoing that, while particular embodiments of the invention have been illustrated and described, various modifications could be made thereto without departing from the spirit and scope of the invention. Therefore, it is not intended that the invention be limited by the specification; instead, the scope of the present invention is intended to be limited only by the appended claims.

What is claimed is:

1. A patient supporting device comprising:

a) a unitary, rigid backboard having a length and a width and including a top side and a bottom side, said top side having a planar surface and said bottom side having a single continuous curvilinear shape which maintains substantially the same cross-section along substantially the length of said backboard and that provides structural support to said top side while providing substantial x-ray translucence to said backboard.

2. The patient supporting device according to claim 1 wherein said single continuous curvilinear shape is formed by a curve comprising two peaks placed at equidistant locations from a trough.

3. The patient supporting device according to claim 2 wherein said curve formed between said two peaks and said trough is defined by a 45 degree angle from the bottom of said trough to the top of each of said two peaks.

4. The patient supporting device according to claim 2 wherein said curve between said two peaks and said trough is at an angular orientation that permits said patient supporting device to be substantially X-ray translucent.

5. The patient supporting device according to claim 4 wherein said angular orientation is in a range between 30 degrees and 60 degrees from the bottom of said trough to the top of each of said two peaks.

6. The patient supporting device according to claim 1 wherein said backboard has a rate of deflection of less than two inches when carrying a one hundred pound load or less and supported at two points.

7. The patient supporting device according to claim 1 wherein said backboard has a rate of deflection of less than 0.2 inches when carrying a three hundred pound load or less and supported at four points.

8. The patient supporting device according to claim 1 wherein said backboard has a rate of deflection of less than 0.3 inches when carrying a four hundred pound load or less and supported at four points.

9. A patient supporting device comprising:

a) a unitary, rigid, X-ray translucent member having a length and a width with a top side, a bottom side, and opposing side portions that define a hollow interior portion, said bottom side forming a single curvilinear shape that maintains substantially the same cross-section along substantially the length of said translucent member and said top side having a planar surface and said hollow interior portion containing an X-ray translucent material.

10. The patient supporting device according to claim 9, wherein said hollow interior portion includes at least two structural supporting regions that contain a greater quantity of said X-ray translucent material than the remainder of said hollow interior portion.

11. The patient supporting device according to claim 9 wherein said rigid, X-ray translucent member includes at least one integral handle attached to said rigid X-ray translucent member.

12. The patient supporting device according to claim 9 wherein said single curvilinear shape disperses said X-ray translucent material into at least two structural supporting regions.

13. The patient supporting device according to claim 12 wherein said structural supporting regions enable said rigid, X-ray translucent member to have a rate of deflection of less than two inches when carrying a one hundred pound load or less and supported at two points.

14. The patient supporting device according to claim 12 wherein said structural supporting regions enable said rigid, X-ray translucent member to have a rate of deflection of less than 0.2 inches when carrying a three hundred pound load or less and supported at four points.

15. The patient supporting device according to claim 12 wherein said structural supporting regions enable said rigid, X-ray translucent member to have a rate of deflection of less than 0.3 inches when carrying a four hundred pound load or less and supported at four points.

16. A method of transporting and X-raying a patient comprising the steps of:

a) providing a unitary, rigid, X-ray translucent backboard having a length and a width comprising a planar top side and a bottom side having a single continuous curvilinear shape which maintains substantially the same cross-section along substantially the length of said backboard and that provides structural support to said planar top side, b) placing a patient on said planar top side;

c) transporting said patient to an X-ray machine; and d) obtaining a medically acceptable X-ray of the patient while said patient is still located on said planar top side.

17. The method according to claim 16 wherein said single curvilinear shape defines at least two structural supporting regions that disperse an X-ray translucent material within an interior core defined by said X-ray translucent backboard.

18. The method according to claim 16 wherein said rigid, X-ray translucent backboard has a rate of deflection of less than two inches when said patient weighs 100 pounds or less and said rigid, X-ray translucent backboard is supported at two points.

19. The method according to claim 16 wherein said rigid, X-ray translucent backboard has a rate of deflection of less than 0.2 inches when said patient weighs 300 pounds or less and said rigid, X-ray translucent backboard is supported at four points.

20. The method according to claim 16 wherein said rigid, X-ray translucent backboard has a rate of deflection of less than 0.3 inches when said patient weighs 400 pounds or less and said rigid, X-ray translucent backboard is supported at four points.

* * * * *